United States Patent

Morigi

[11] Patent Number: 5,304,149
[45] Date of Patent: Apr. 19, 1994

[54] MEDICAL DEVICE WITH A LOCKABLE NEEDLE SHIELD

[75] Inventor: Adriano Morigi, Rutherford, N.J.
[73] Assignee: Becton, Dickinson and Company, Franklin Lakes, N.J.
[21] Appl. No.: 897,632
[22] Filed: Jun. 12, 1992
[51] Int. Cl.⁵ ............................................. A61M 5/00
[52] U.S. Cl. .................................... 604/192; 604/198
[58] Field of Search ............... 604/110, 187, 192, 263, 604/198

[56] References Cited

U.S. PATENT DOCUMENTS

| | | | |
|---|---|---|---|
| 4,573,976 | 3/1986 | Sampson et al. | 604/198 |
| 5,053,018 | 10/1991 | Talonn et al. | |
| 5,106,380 | 4/1992 | Lobello | 604/198 |

Primary Examiner—John D. Yasko
Attorney, Agent, or Firm—Richard J. Rodrick

[57] ABSTRACT

A medical device includes a barrel with proximal and distal ends. A needle extends from the distal end of the barrel and terminates in a point. A shield is coaxially and rotationally mounted on the barrel. This shield is axially movable between a retracted position in which the needle point is exposed and an extended position in which the needle point is covered. The device includes locking elements associated with the barrel and the shield. These locking elements are responsive to a combined rotational and axially distal movement of the shield, when the shield is at an extended and unlocked position, for locking the shield on the barrel at the extended position. These locking elements prevent subsequent rotational and axial movement of the shield on the barrel.

9 Claims, 5 Drawing Sheets

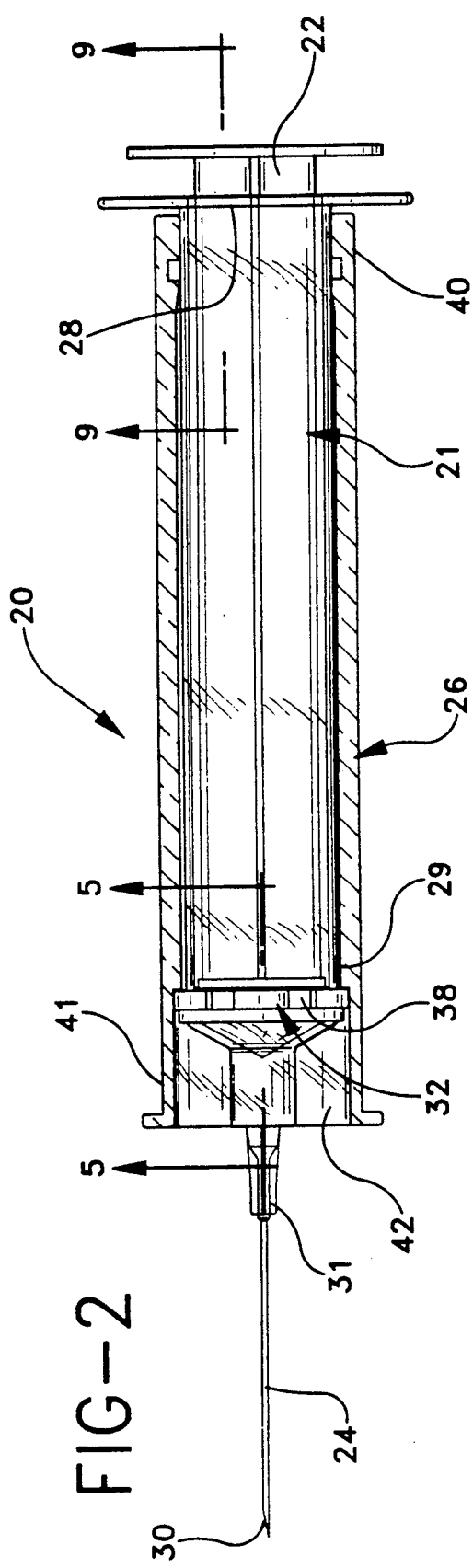
FIG-2
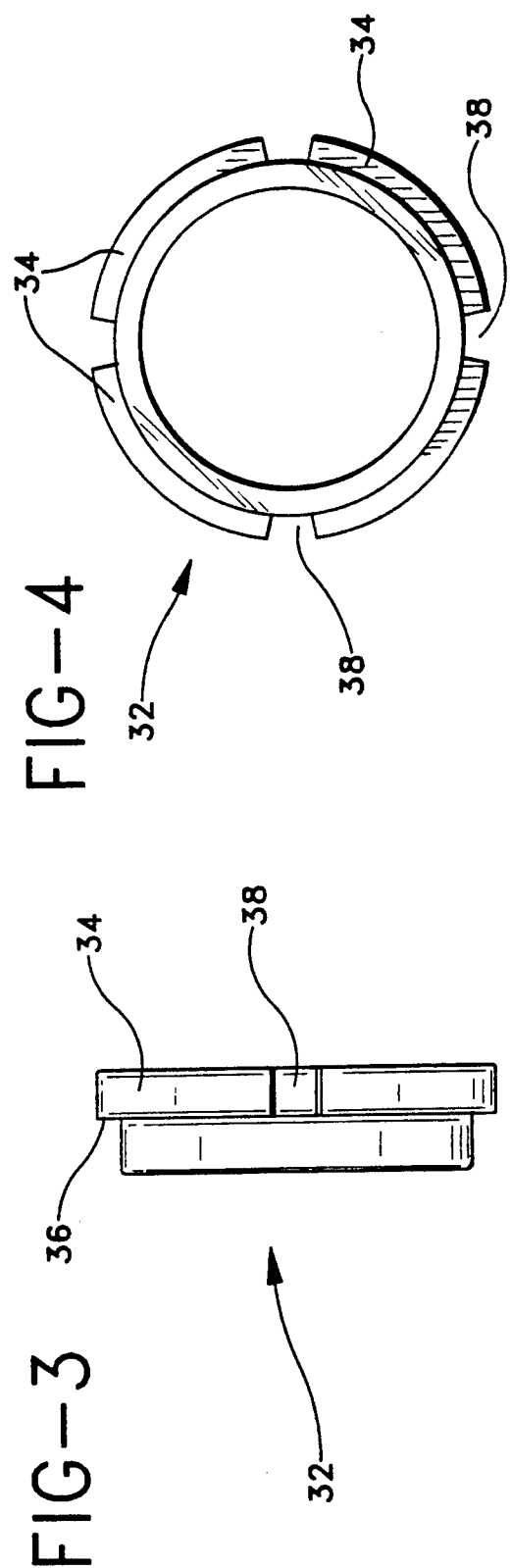
FIG-4
FIG-3

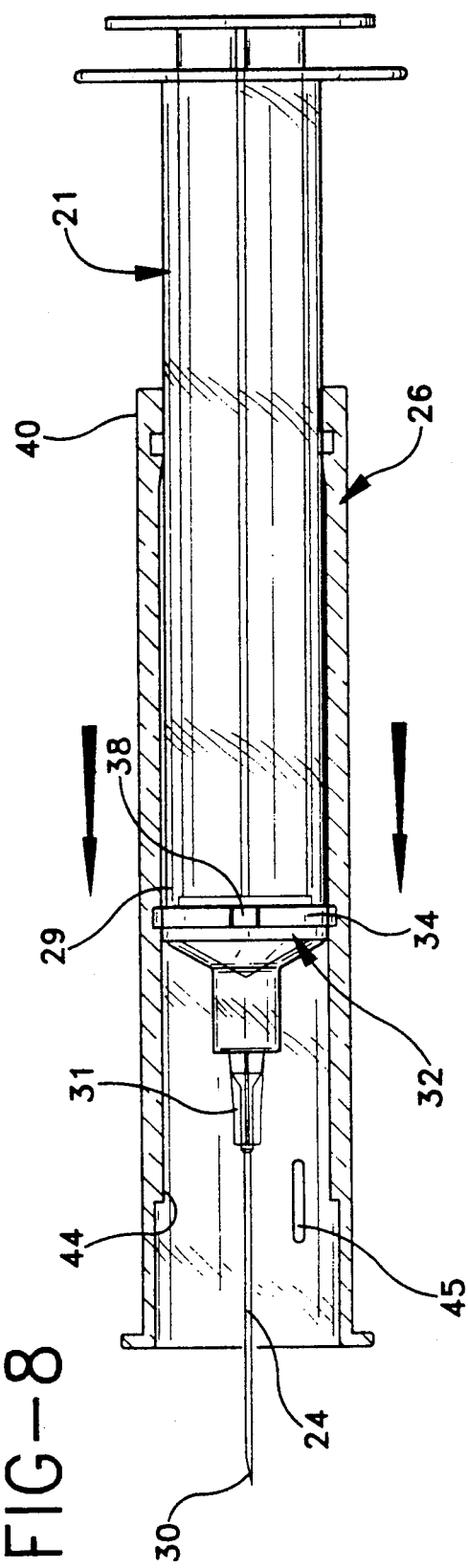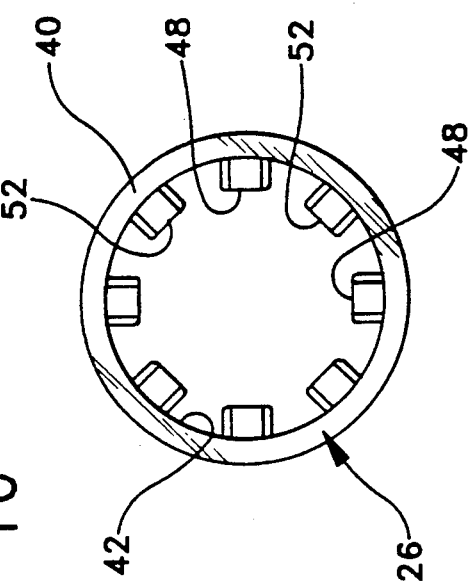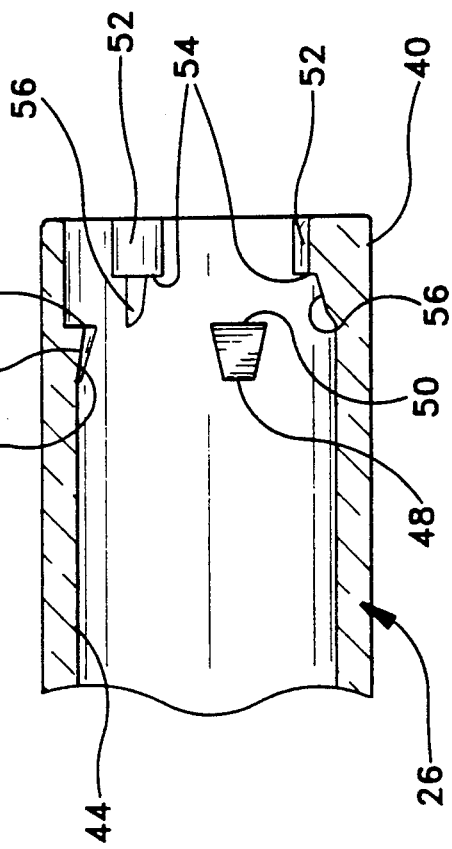

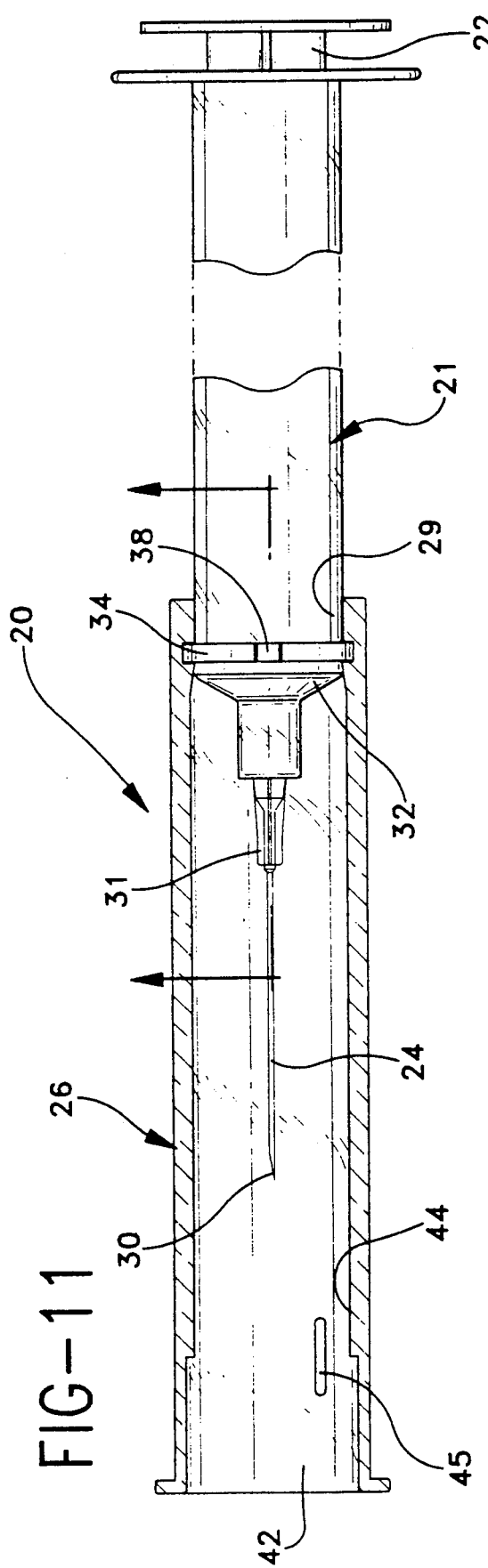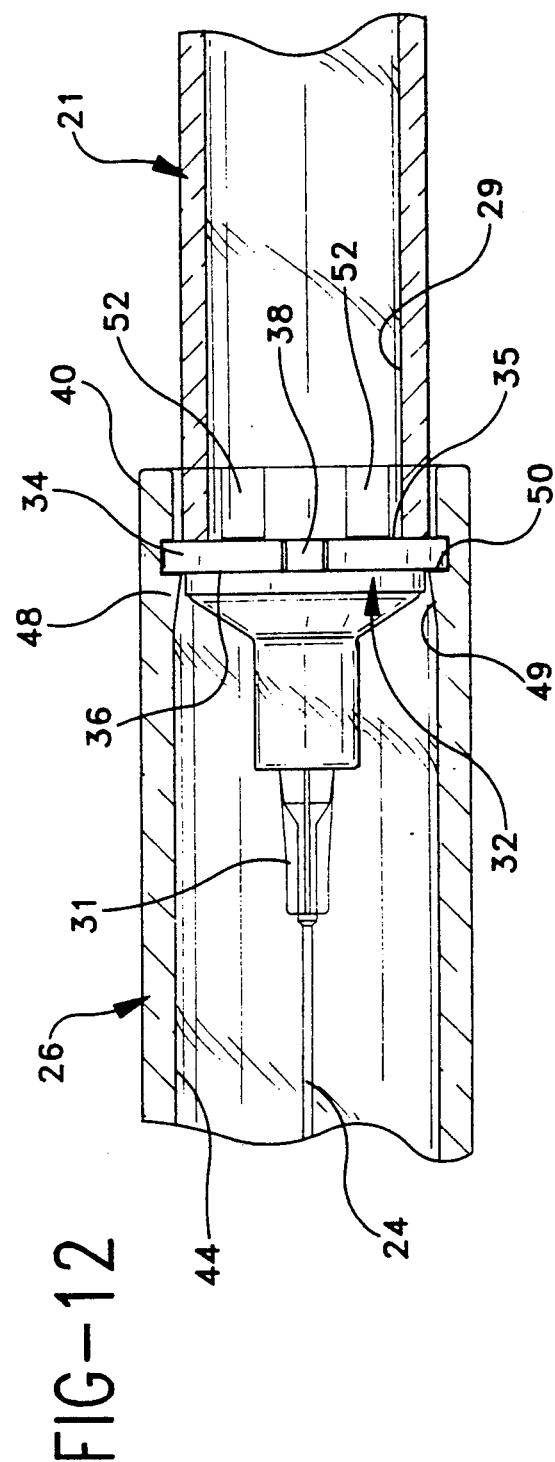

MEDICAL DEVICE WITH A LOCKABLE NEEDLE SHIELD

BACKGROUND OF THE INVENTION

1. Field of the Invention

The present invention relates to a medical device of the type having a needle and a shield for covering a point of the needle after the device is used. The present invention more particularly concerns a syringe-type device with a shield for the needle, the shield being operatively attached to the syringe so that it may be locked in a position which covers the needle point thereby protecting personnel who work with these types of medical devices.

2. Background Description

Personnel in hospitals, medical laboratories, doctors offices and the like face the risk of being stuck with sharp points on needles, blades and other devices used for bodily invasive purposes. After any of these sharp-pointed devices are used in an invasive procedure, they may be contaminated as a result of any infectious diseases or conditions carried by the patient. The infectious disease may be transmitted to any person who is working with these devices and who inadvertently or carelessly gets stuck.

Many sharp-pointed medical devices, such as needles, are originally packaged with a cover which is removable just prior to use. Problems have arisen in the past when medical personnel have attempted to re-shield the device after use. Medical personnel frequently have stuck themselves while attempting these re-shielding procedures and, as a result, re-shielding is not recommended in most of these procedures. To avoid these circumstances, sharp-pointed medical devices are being designed with built-in shields. These shields are normally attached to, but moved out of the way of, the sharp point during use of the medical device. After use, the shield is generally movable, in some fashion, to cover the sharp point so that no one may be stuck.

In U.S. Pat. No. 5,053,018, a syringe device is described which includes a movable needle shield. In this patent, the shield is locked at the extended position at which the shield covers the needle. The benefits of using a rotational movement to lock the shield in place are explained in this patent.

Although medical devices have been described with lockable shields, in which the shield is movable in one or more directions, further improvements are still being sought and are needed in this field. These sought-after needs include improvements in ease of use, efficiency of manufacture and assembly, lower costs of manufacture and packaging and compatibility with existing procedures in the various medical facilities. The present invention represents such an improvement.

SUMMARY OF THE INVENTION

The medical device of the present invention includes a barrel with proximal and distal ends. A needle extends from the distal end of the barrel and terminates in a point. A shield is coaxially and rotationally mounted on the barrel. This shield is axially movable between a retracted position in which the needle point is exposed and an extended position in which the needle point is covered. There are means associated with the barrel and the shield for locking the shield on the barrel at the extended position. These means are responsive to a combined rotational and axially distally movement of the shield when the shield is at an extended and unlocked position. In the locked position, the shield is prevented from being subsequently rotated and axially moved on the barrel.

In a preferred embodiment of the present invention, the medical device with the movable shield mounted thereon, with the locking elements as described above, is a syringe.

In accordance with the principles of the present invention, the built-in, movable shield is in a retracted position during use of the device, and then may be readily moved in an easy step to cover the sharp point after use. The features of the present invention permit the shield to be slid along the barrel with little force and effort. The elements of the medical device of the present invention may be manufactured in a way in which acceptable break-away and lock-in forces are provided, thereby allowing looser tolerances of the manufactured components. Further, the twist-pull motion under which the shield is locked over the sharp point is easily performed by the users of these medical devices.

BRIEF DESCRIPTION OF THE DRAWINGS

FIG. 2 is a cross sectional view of the device of FIG. 1 taken along line 2—2 thereof;

FIG. 3 is an enlarged side elevational view of the collar included on the device of FIG. 1;

FIG. 4 is an enlarged bottom plan view of the collar of FIG. 3;

FIG. 8 is a cross-sectional view of the medical device of the present invention, similar to FIG. 2, but illustrating the shield released from the retracted position and moved distally toward its extended position;

FIG. 9 is an enlarged sectional view of the proximal end of the shield taken along line 9—9 of FIG. 2 and illustrating the various elements for locking the shield in the extended position;

FIG. 10 is an enlarged bottom plan view of the shield of FIG. 9 illustrating the arrangement of the various locking elements;

FIG. 11 is a cross-sectional view similar to the view of FIG. 8, illustrating the shield locked in the extended position and covering the needle point; and FIG. 12 is an enlarged cross-sectional view taken along line 12—12 of FIG. 11 and illustrating the locking arrangement of the collar and the locking elements on the interior surface of the shield.

DETAILED DESCRIPTION

Figure 1:
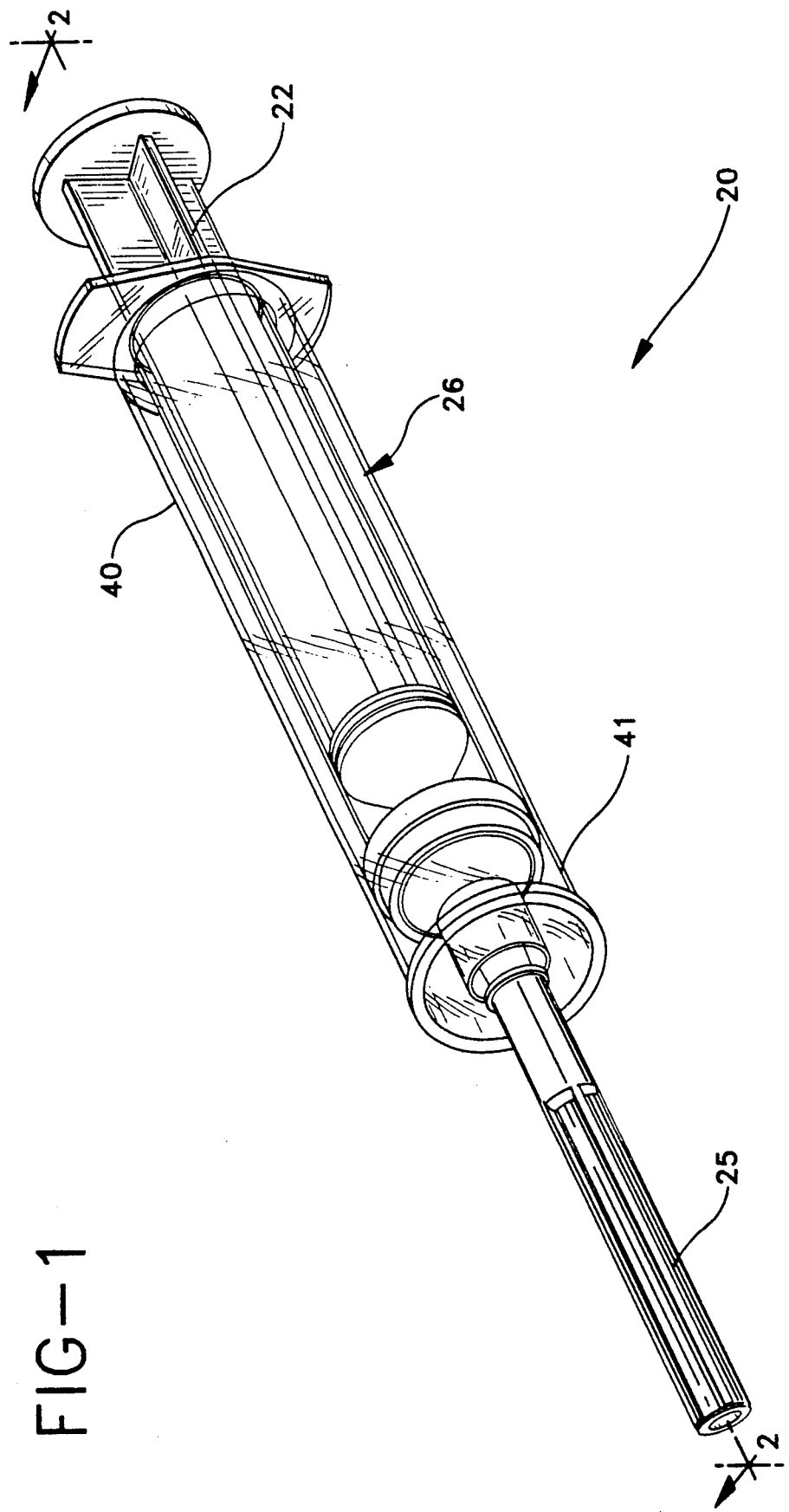
FIG. 1 is a perspective view of the preferred medical device of the present invention in the form of a syringe.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

With respect to the invention described herein, use of the word "proximal" with respect to an element refers to the direction closest to the user, while use of the word "distal" with respect to an element refers to a direction away or furthest from the user.

Referring now to FIGS. 1 and 2, a syringe assembly 20 is illustrated. The general components of this syringe assembly include a barrel 21, and plunger 22, a needle 24, a removable protective cover 25 for the needle and a movable shield 26 coaxially and rotationally mounted on barrel 21.

Barrel 21 has a proximal end 28 which is open so that plunger 22 is insertable into the barrel and is slidable therein so that fluid may be expelled from or aspirated to the interior of the barrel in well-known fashion. The opposite end of barrel 21 is the distal end 29 and, as can be seen, needle 24 extends from this distal end of the barrel and terminates in a needle point 30. In conventional fashion, needle 24 is typically mounted in a hub 31 which, in turn is connected to distal end 29 of the barrel either in permanent or removable fashion. In order to facilitate the locking features of the present invention, a collar 32 is preferably included at distal end 29 of the barrel. This collar preferably is a separate component as seen more particularly in FIGS. 3 and 4, which is attachable to the end of the barrel or may be integrally formed as part of the distal end of the barrel itself.

Collar 32 preferably includes an annulus 34 in the shape of a cylindrical ring. When mounted on or formed as part of distal end 29 of the barrel, annulus 34 preferably has a larger diameter than the outside diameter of the barrel, thereby forming a raised member around the barrel. Defining annulus 34 are two substantially planar surfaces 35 and 36, which are substantially parallel to each other. Extending through annulus 34 between these opposed surfaces is a series of slots 38. Although there are four substantially equally spaced slots 38 illustrated in the drawings, it is understood that only one slot could perform the functions of the present invention, with a plurality of these slots merely being preferable. These slots are open-ended at the outside radial surface of annulus 34.

Figure 6:
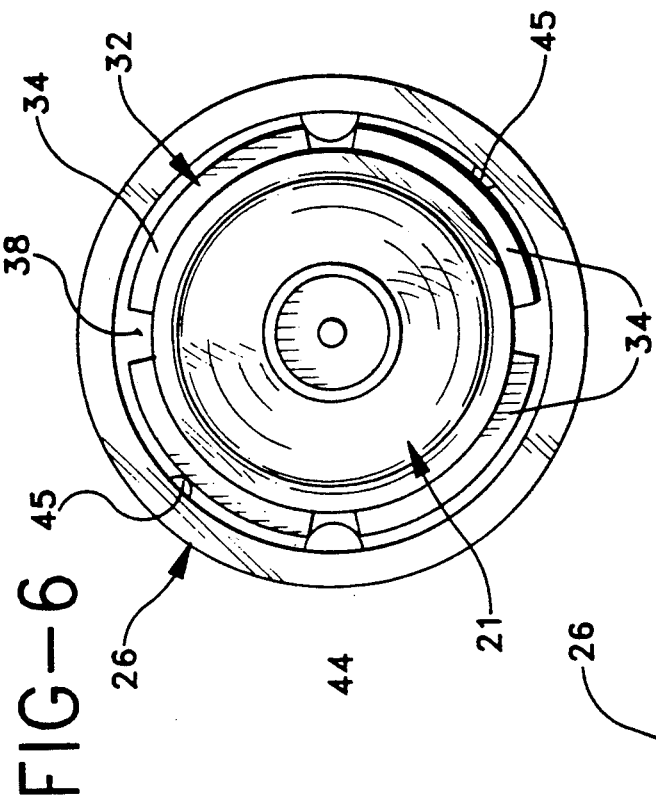
FIG. 6 is an enlarged bottom plan view of the arrangement between the shield and the collar when the shield is in the retracted position.
Figure 5:
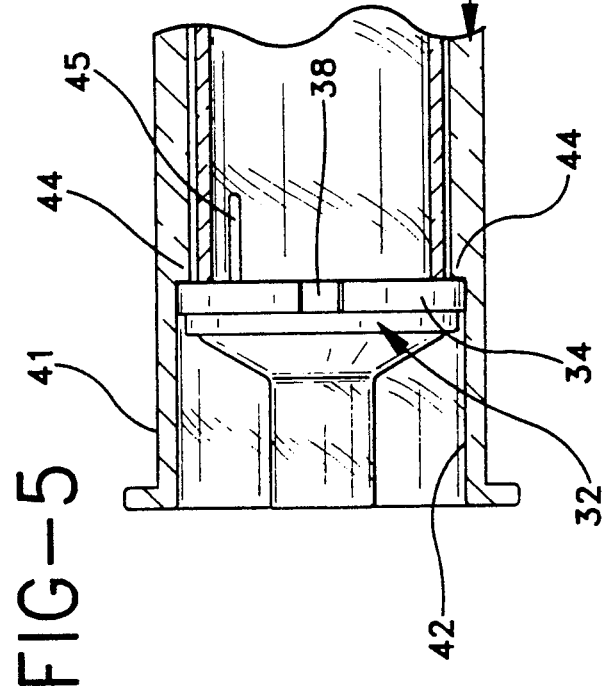
FIG. 5 is an enlarged partial sectional view taken along 5—5 of FIG. 2 illustrating the arrangement of the shield in the retracted position with respect to the barrel and collar.

Turning now to FIGS. 5 and 6, taken in conjunction with FIGS. 1 and 2, shield 26 is illustrated in its retracted position. In this configuration, shield 26 is slid over and virtually covers barrel 21 so that proximal end 40 of the shield is closer to proximal end 28 of the barrel. Distal end 41 of the shield is arranged at or near distal end 29 of the barrel so that needle 24 may be exposed once needle cover 25 is removed.

Extending inwardly from the interior surface 42 of the shield is a pair of ribs 44. These ribs extend substantially along the entire length of the interior surface of the shield between the distal and proximal ends thereof. Although there are two such ribs illustrated in the drawings spaced about 180° apart, it is understood that the inclusion of only one such rib would serve the purposes of the present invention.

Figure 7:
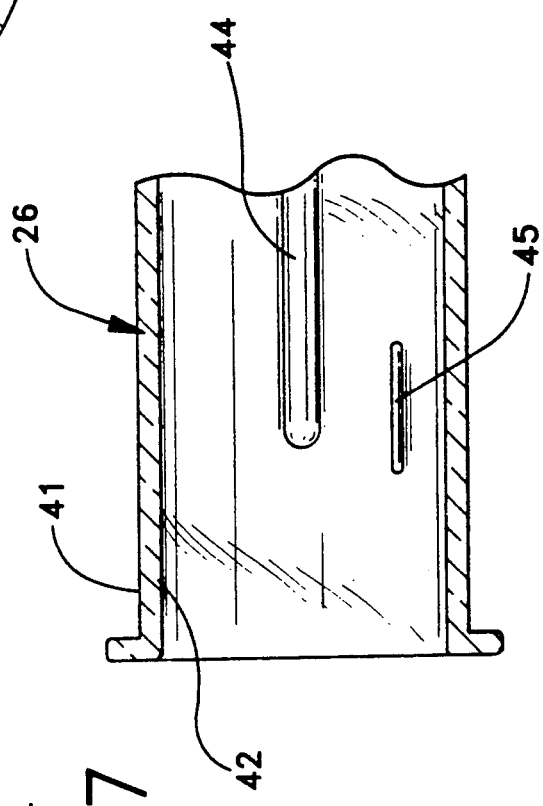
FIG. 7 is an enlarged sectional view similar to FIG. 5 with the shield rotated about 90° from the orientation illustrated in FIG. 5.

As more clearly seen in FIGS. 5,6 and 7, there are two additional projections 45 extending radially inwardly from interior surface 42 of the shield. Projections 45 are preferably much shorter in axial length than ribs 44, and are located at distal end 41 of the shield. While there are two such projections 45 illustrated in the drawings, it is understood that the inclusion of only one projection would serve the purposes of the present invention. It can be seen that projections 45 are rotationally spaced from ribs 44, approximately one eighth of a turn.

When the syringe of the present invention is assembled, and shield 26 is in the retracted position as seen in FIGS. 1 and 2, projections 45 are positioned within opposed slots 38 of collar 32. This arrangement temporarily locks the shield in the retracted position on the barrel since the shield cannot be readily rotated without applying a rotational force. Also, in this arrangement the shield cannot be moved axially because the distal ends of ribs 44 contact surface 35 of annulus 34 thereby preventing movement of the shield in the distal direction. Further, the shield cannot move in a proximal direction because the conventional finger flange at the proximal end of the barrel prevents such movement.

After the syringe has been used, and it is desired to cover needle point 30, the user actuates the slidable shield by applying a rotational movement to the shield with respect to the barrel. Sufficient rotational torque is applied by the user until locking projections 45 on the interior of the shield snap out of slots 38 on the annulus of the collar. Such rotation continues until ribs 44 on the interior surface of the shield snap into slots 38, as more clearly seen in FIGS. 5 and 6. Typically, the rotational spacing between ribs 44 and projections 45 is about one eighth of a turn, although such rotational spacing may vary according to design of the medical device. Once ribs 44 are aligned so that they are engaged within the slots of the annulus of the collar, the shield is then slidable in an axial direction over the barrel due to the guiding arrangement provided by the alignment of the ribs in the slots.

As seen in FIG. 8, shield 26 has been moved axially from its retracted position in the direction toward its extended position, as indicated by the arrows alongside the shield, in order to eventually cover completely needle 24, including needle point 30. Once at the fully extended position, the shield is firmly locked in position with respect to the barrel so that axial movement in either direction, as well as rotational movement, is prevented. To achieve this locking capability, reference is now made to FIGS. 9-12, in particular.

At proximal end 40 of shield 26, in the particular embodiment being described, there are four equally spaced locking protuberances 48 extending inwardly from interior surface 42 of the shield. These locking protuberances preferably are arranged to match with, in size and number, slots 38 in the annulus of the collar. Even though four such protuberances are shown, it is understood that only one such protuberance may be used to serve the purposes of the present invention.

Two of the four locking protuberances are axially aligned with guiding ribs 44 so that as the ribs slide through slots 38, all of the protuberances are aligned with slots 38 in the collar so that they may pass therethrough. Each protuberance 48 is dimensionally sized so that it may freely pass through the slots in the collar. Further, each protuberance is defined by an inclined surface 49 and a relatively flat locking surface 50 which extends substantially perpendicular to the longitudinal axis of the shield. In this regard, protuberances 48 take on a wedge-shaped configuration as more clearly seen in FIGS. 9 and 11.

In addition to the protuberances projecting from the interior surface of the shield, there are additional locking elements of the present invention also projecting inwardly from the interior of the shield at its proximal end. More specifically, there are four locking stops 52 located proximally from protuberances 48 and spaced substantially equally around the interior surface of the shield. Stops 52 preferably are also rotationally spaced from the protuberances. While there are four such stops illustrated in the drawings, it is understood that this number of stops is merely preferable. For purposes of the present invention, there may be only one stop. The stop may be in the form of a stepped shoulder either partially or completely around the interior surface of the shield. Each stop 52 illustrated in the drawings includes a substantially flat surface 54 which lies substantially perpendicular to the longitudinal axis of the shield. In this respect, surfaces 54 of stops 52 lie substantially parallel to surfaces 50 of protuberances 48. Further, the spacing between surfaces 50 and 54 is such that the distance is slightly greater than the height of annulus 34 of the collar so that the annulus may be engageable to these respective surfaces for locking purposes.

Extending axially from locking stops 52 in the direction toward protuberances 48 are other locking elements, in the form of detents 56. These detents also extend inwardly from the interior surface of the shield and are sized to fit within and engage slots 38 in the annulus of the collar. It can be seen particularly in FIG. 9, that detents 56 have a slightly rounded configuration which facilitates their being snapped into slots 38 during rotation of the shield after protuberances 48 have passed through the slots of the collar. As with stops 52, detents 56 are positioned at a location rotationally spaced from protuberances 48, and this rotational spacing is typically about one eighth of a turn.

FIGS. 11 and 12 illustrate the shield at the extended, locked position. As the user slides shield 26 in an axially distal direction (as previously described with respect to FIG. 8), guiding ribs 44 cause protuberances 48 to pass through the slots in the collar when the shield has reached its extended position. At that point, and in order to lock the shield in the extended position, the shield is rotated and at the same time also moved in an axially distal direction, in a "twist-pull" motion. This combined rotational and axially distal movement causes detents 56 to snap into slots 38 in the annulus of the collar. When this occurs as a result of this combined axial and rotational movement, the shield is locked at the extended position, thereby assuring that needle point 30 is fully covered by the locked shield.

Locking of the shield with respect to the barrel is achieved in three different, but yet, independent respects. Firstly, retrograde movement of the shield with respect to the barrel is prevented because surfaces 50 of protuberances 48 engage locking surface 36 on the annulus of the collar. Secondly, further axial movement in the forward or distal direction is prevented in this arrangement because faces 54 of stops 52 engage locking surface 35 on the annulus of the collar. Thirdly, detents 56 are positioned within slots 38 around the annulus of the collar thereby preventing rotational movement of the shield with respect to the barrel.

The components of this particular syringe assembly are easily manufactured, and, except for the collar and shield, are conventional. The collar and the shield are preferably made out of plastic and, as a result of the particular features of the present invention, acceptable break away and lock-in forces are readily achieved, and looser tolerances are permitted for the manufacture and assembly of the various components.

Thus, the present invention provides a shielded medical device in which the point of the needle may be covered after use by a slidable and rotational shield adapted to be locked when the shield is at the extended position.

What is claimed is:

1. A medical device comprising:
   a barrel having proximal and distal ends;
   a needle extending from the distal end of the barrel and terminating in a point;
   a shield coaxially and rotationally mounted on said barrel, said shield being axially movable between a retracted position in which said needle point is exposed and an extended position in which said needle point is covered;
   means associated with said barrel and said shield and responsive to a combined rotational is axially distal movement of said shield, when said shield is at an extended and unlocked position, for locking said shield on said barrel at said extended position and for preventing subsequent rotational and axial movement of the shield on the barrel, said means including a collar at the distal end of the barrel, said collar forming a raised annulus around an outside surface of the barrel, said collar having a first locking surface and a second locking surface and at least one slot extending through said collar between said surfaces, said means further including at least one locking protuberance extending inwardly from an interior surface of said shield, said protuberance being sized to pass through the slot in said collar when the shield is in said extended position and, upon rotation of said shield, said protuberance being adapted to engage the first locking surface of said collar thereby preventing retrograde axial movement of said shield with respect to said barrel;
   means associated with the shield for guiding the movement of the shield from the retracted to the extended position and for facilitating the function of the means for locking the shield on said barrel at said extended position; and
   means associated with the shield for preventing movement of the shield from its retracted position toward the extended position but being responsive to rotation of said shield with respect to said barrel for permitting such movement, said means for preventing including a locking projection extending inwardly from the interior of said shield and spaced rotationally from said means for guiding, said projection adapted to engage said slot when the shield is in its retracted position and, upon rotation of said shield with respect to said barrel, to become removed from said slot whereby said shield is unlocked for movement to its extended position.

2. The device of claim 1 wherein said means includes at least one stop extending inwardly from the interior surface of said shield, said stop adapted to engage the second locking surface of said collar when the shield is in said extended position thereby preventing distal axial movement of said shield with respect to said barrel.

3. The device of claim 2 wherein said means includes at least one detent extending inwardly from the interior surface of said shield, said detent adapted to fit within and engage the slot in said collar thereby preventing rotational movement of said shield with respect to said barrel.

4. The device of claim 3 wherein said collar has an axially extending height and wherein said protuberance and said stop are axially spaced on the interior surface of said shield a distance slightly greater than the height of said collar so that the protuberance and the stop are engageable with the respective surfaces.

5. The device of claim 4 wherein said detent is positioned on the interior surface of said shield at a location axially between said protuberance and said stop, but at a location rotationally spaced from said protuberance so that said combined rotational and axially distal movement of said shield causes the protuberance to pass through the slot and the detent to fall into the slot.

6. The device of claim 3 wherein the collar has a plurality of angularly spaced slots and wherein the means includes a plurality of said protuberances and a plurality of detents, said protuberances and said detents arranged around the interior surface of said shield at substantially the same angular spacing as said slots, with said protuberances and said detents being rotationally spaced from each other.

7. The device of claim 1 wherein said means for guiding includes at least one rib extending inwardly from the interior surface of said shield, said rib being elongate and axially aligned with protuberance, said rib adapted to slidably fit within said slot and to guide said protuberance into said slot when the shield is moved to the extended position.

8. A syringe assembly comprising:
a barrel having proximal and distal ends and outside surface;
a plunger slidably within the barrel;
a needle extending from the distal end of the barrel and terminating in a point;
a shield coaxially and rotationally mounted with respect to said barrel, said shield being axially movable between a retracted position in which said needle point is exposed and an extended position in which said needle pint is covered;
a collar at the distal end of said barrel, said collar forming a raised annulus around the outside surface of said barrel and having a first locking surface, a second locking surface and at least one slot extending through the collar between the surface;
means associated with said collar and said shield and responsive to a combined rotational and axially distal movement of said shield, when said shield is at an extended and unlocked position, for locking said shield at said extended position and for preventing subsequent rotational and axial movement of the shield with respect to said barrel;
means associated with the shield for guiding the movement of the shield from the retracted to the extended position and for facilitating the function of the means for locking the shield at the extended position; and
means associated with the shield for preventing movement of the shield from its retracted position toward the extended position but being responsive to rotation of said shield with respect to said barrel for permitting such movement, said means for preventing including a locking projection extending inwardly from the interior of said shield and spaced rotationally from said means for guiding, said projection adapted to engage said slot when the shield is in its retracted position and, upon rotation of said shield with respect to said barrel, to become removed from said slot whereby said shield is unlocked for movement to its extended position.

9. The assembly of claim 8 further including a removable protective cover which covers said needle point when the shield is at the retracted position.

* * * * *